United States Patent [19]

Garner et al.

[11] 4,046,776
[45] Sept. 6, 1977

[54] HETEROCYCLIC SUBSTITUTED LACTONE COMPOUNDS

[75] Inventors: Robert Garner, Bury, England; Jean-Claude Petitpierre, Kaiseraugst, Switzerland

[73] Assignee: Ciba-Geigy Corporation, Ardsley, N.Y.

[21] Appl. No.: 564,383

[22] Filed: Apr. 2, 1975

[30] Foreign Application Priority Data

Apr. 9, 1974   United Kingdom ............... 15645/74

[51] Int. Cl.$^2$ ................ C07D 209/04; C07D 261/20; C07D 405/04
[52] U.S. Cl. ............... 260/326.14 R; 260/293.58; 260/287 T; 260/326 N; 260/315; 260/268 BC; 260/295 F; 260/294.8 C; 260/268 TR; 260/326.34; 544/58; 544/143; 544/144; 548/336; 548/374; 544/141; 544/142; 544/131; 544/120; 544/128; 544/167; 544/172; 106/23; 106/288 Q
[58] Field of Search ............... 260/247.2 B, 268 BC, 260/293.58, 326.14 R, 287 T, 326 N, 315; 106/21, 23, 26, 289, 288 Q

[56] References Cited

U.S. PATENT DOCUMENTS

| | | | |
|---|---|---|---|
| 3,540,909 | 11/1970 | Lin .................... | 260/326.14 |
| 3,540,910 | 11/1970 | Lin .................... | 260/326.14 |
| 3,540,911 | 11/1970 | Lin .................... | 260/326.14 |
| 3,540,912 | 11/1970 | Lin .................... | 260/326.14 |
| 3,540,913 | 11/1970 | Lin .................... | 260/326.14 |
| 3,549,646 | 12/1970 | Hamilton et al. ........ | 260/294 |
| 3,649,649 | 3/1972 | Orita et al. ............ | 260/343.3 |
| 3,725,416 | 4/1973 | Yamamoto et al. ........ | 260/293.58 |
| 3,812,146 | 5/1974 | Farber et al. .......... | 260/326.14 |
| 3,829,322 | 8/1974 | Ozutsumi et al. ........ | 260/326.14 |
| 3,901,918 | 8/1975 | Koga et al. ............ | 260/335 |

FOREIGN PATENT DOCUMENTS

| | | | |
|---|---|---|---|
| 2,163,658 | 7/1972 | Germany ............ | 260/293.58 |
| 2,259,409 | 6/1973 | Germany ............ | 260/293.58 |
| 48-21330 | 6/1973 | Japan | |

OTHER PUBLICATIONS

Derwent Japanese Patents Reports, vol. 74, No. 5 (May 3, 1974).

Primary Examiner—John M. Ford
Attorney, Agent, or Firm—Karl F. Jorda; Edward McC. Roberts; Michael W. Glynn

[57] ABSTRACT

Lactone compounds of the formula

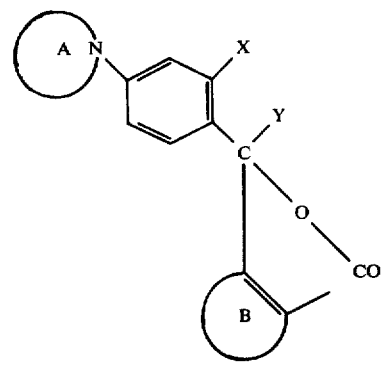

wherein
X represents alkyl with 1 to 12 carbon atoms, alkoxy with 1 to 12 carbon atoms or acyloxy with 2 to 12 carbon atoms,
Y represents an optionally substituted 2-pyrrolyl, 3-indolyl or 3-carbazolyl radical,
the nitrogen ring A represents a heterocyclic radical which optionally includes a further hetero atom as a ring member and the ring B represents a 6-membered aromatic or heterocyclic ring which may have an aromatic condensed ring and both the ring B and the condensed ring may be substituted. These lactone compounds are particularly useful as color formers which give intense green-blue, blue or violet-blue colors when they are brought into contact with an electron-accepting co-reactant.

11 Claims, No Drawings

HETEROCYCLIC SUBSTITUTED LACTONE COMPOUNDS

The invention provides novel heterocyclic substituted lactone compounds which can give intense blue colours when they are contacted with an electron accepting co-reactant. The invention specifically relates to lactone compounds of the phthalide and azaphthalide series having a 3-phenyl group which contains in the para position a nitrogen heterocyclic residue attached to the benzene ring through the nitrogen atom; a process for the manufacture of such lactone compounds and their use as colour formers in pressure-sensitive or thermoreactive copying materials.

The new lactone compounds according to the invention corrensponds to the formula

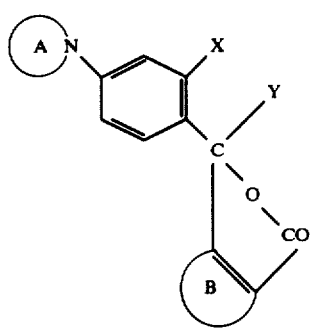

(1)

wherein
X represents alkyl with 1 to 12 carbon atoms, alkoxy with 1 to 12 carbon atoms or acyloxy with 2 to 12 carbon atoms,
Y represents an optionally substituted 2-pyrrolyl, 3-indolyl or 3-carbazolyl radical,
the nitrogen ring A represents a heterocyclic radical which optionally includes a further hetero atom as a ring member and the ring B represents a 6-membered aromatic or heterocyclic ring which may have an aromatic condensed ring and both the ring B and the condensed ring may be substituted. The radical X may represent a straight or branched chain alkyl group such as methyl, ethyl, isopropyl, sec-butyl, tert.butyl, hexyl, octyl or dodecyl; a straight or branched chain alkoxy group such as methoxy, ethoxy, isopropoxy, tert.butoxy, octoxy or dodecyloxy; an acyloxy group such as the radical of an alkane carboxylic acid, preferably an alkanoyloxy group having 2 to 4 carbon atoms e.g. acetoxy or propionyloxy.

The heterocyclic radical Y may be an optionally substituted 2-pyrrolyl, 3-indolyl or 3carbazolyl radical wherein optional substituents may be bound at the nitrogen atom or at a carbon atoms of the heterocycle or in the benzene rings, if present. Said substituents may be alkyl having 1 to 12 carbon atoms, alkenyl having at most 12 carbon atoms, acyl with 2 to 12 carbon atoms, phenyl or benzyl both optionally substituted by halogen, nitro, alkyl having 1to 4 carbon atoms or alkoxy having 1 to 4 carbon atoms. The benzene rings of the heterocyclic system Y may also contain halogen, nitro or an amino group which may be mono- or disubstituted by alkyl with 1 to 6 carbon atoms, such as a dimethylamino, diethylamino or n-hexylamino. Halogen in each occurrence in the definitions of the substituents preferably stands for fluorine or bromine or especially chlorine.

The nitrogen ring A represents a heterocyclic radical which is attached to the benzene ring through the nitrogen atom. The heterocyclic radical may have 3 to 12 or 15, preferably 5 or 6 ring members, wherein 1 or 2 hetero atoms may be included as ring members. It is for instance a pyrrolidinyl, piperidino, pipecolino, perhydroazepinyl, hexamethyleneiminyl, heptamethyleneiminyl, octamethyleneiminyl, 1,2,3,4-tetrahydroquinolinyl, indolinyl, phthalimidinyl or hexahydrocarbazolyl group, or when the hetero ring includes a further hetero atom a morpholino, thiomorpholino, piperazino, N-alkylpiperazino or N-alkylimidazolino with 1 to 4 carbon atoms in each alkyl part, N-phenylpiperazino, pyrazolino or 3-methylpyrazolino group. Preferably, the nitrogen ring A forms a piperidino and most preferably a pyrrolidinyl radical.

As 6-membered aromatic ring, B represents preferably a benzene nucleus which is unsubstituted or substituted by halogen such as chlorine or bromine, nitro or an optionally substituted amino group as hereinbefore defined. As 6-membered heterocyclic ring, B represents mainly a nitrogen containing heterocycle of aromatic character such as a pyridine or pyrazine ring. The ring B may also contain a condensed aromatic ring, preferably a benzene ring representing thus for example a naphthalene or quinoline ring.

The preferred 6-membered aromatic or heterocyclic radicals represented by B are 2,3-pyridino, 2,3-pyrazino, 2,3-naphthaleno or especially 1,2-benzo which is unsubstituted or substituted by nitro or four chlorine atoms.

Practically important groups of the compounds of the formula (1) may be defined by the following formula

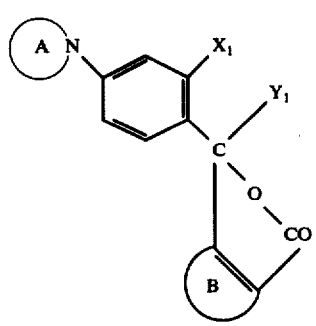

(2)

wherein
$X_1$ represents alkyl with 1 to 4 carbon atoms, alkoxy with 1 to 8 carbon atoms, or acyloxy with 2 to 8 carbon atoms,
$Y_1$ represents a heterocyclic radical selected from (2.1)     (2.2)

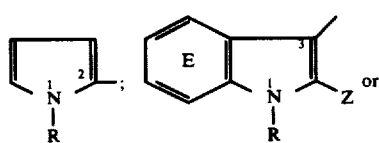

or

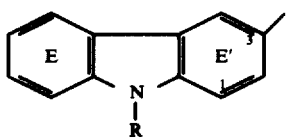

(2.3)

R represents hydrogen, alkyl with 1 to 12 carbon atoms, alkenyl having at most 12 carbon atoms, acyl with 2 to 12 carbon atoms, phenyl or benzyl, said phenyl or benzyl radicals may be substituted by halogen, nitro, methyl or methoxy, Z represents hydrogen, alkyl with 1 to 12 carbon atoms or phenyl, the benzene rings E and E', independently of the other, may be further substituted by alkyl having 1 to 4 carbon atoms, alkoxy having 1 to 4 carbon atoms, halogen or nitro, the nitrogen ring A represents a heterocyclic radical which optionally includes a further hetero atom as a ring member and the ring $B_1$ represents an optionally substituted benzene, naphthalene, pyridine or pyrazine ring.

Among the compounds of the formula (2) the most practical compounds may be defined by the following formula

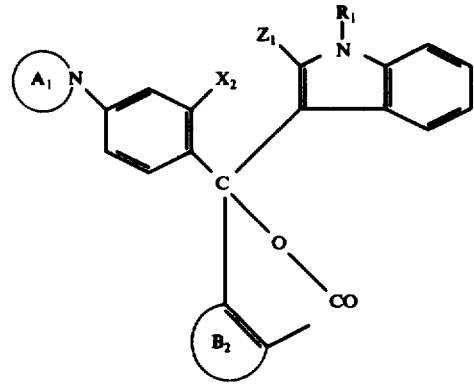

(3)

wherein $X_2$ represents alkyl with 1 to 4 carbon atoms, alkoxy with 1 to 4 carbon atoms or alkanoyloxy with 2 to 4 carbon atoms, $Z_1$ represents hydrogen, alkyl with 1 to 4 carbon atoms or phenyl, $R_1$ represents a hydrogen, alkyl with 1 to 12 carbon atoms, alkanoyl with 2 to 4 carbon atoms or benzyl, the nitrogen ring $A_1$ represents 5- or 6-membered heterocyclic radical, especially a pyrrolidino or piperidino ring and the ring $B_2$ represents a benzene, naphthalene or pyridine ring, wherein the benzene ring of $B_2$ is unsubstituted or substituted by chlorine, bromine or nitro.

Further particularly useful phthalide compounds falling under the lactones of the formulae (1) and (2) may be represented by the formula (4)

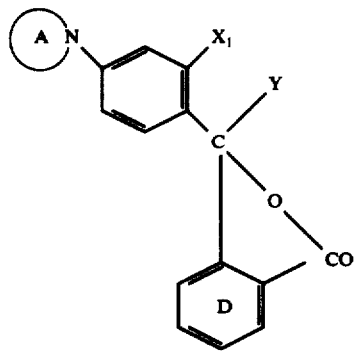

wherein

A and $X_1$ have the given meanings, $Y_2$ represents a radical selected from (4.1)        (4.2)

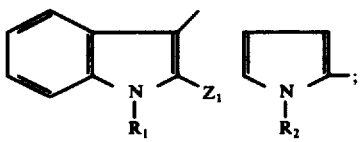

(4.3)

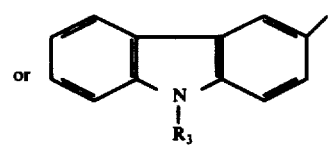

$R_1$ represents hydrogen, alkyl with 1 to 12 carbon atoms, alkanoyl with 2 to 4 carbon atoms or benzyl, $R_3$ represents hydrogen, alkyl with 1 to 4 carbon atoms or phenyl, $R_2$ represents hydrogen or alkyl with 1 to 4 carbon atoms, $Z_1$ represents hydrogen, alkyl with 1 to 4 carbon atoms or phenyl and the benzene ring D may be substituted by nitro or 1 to 4 halogen atoms.

Of special interest are phthalide compounds falling under formulae (1) to (4) and having the formula (5)

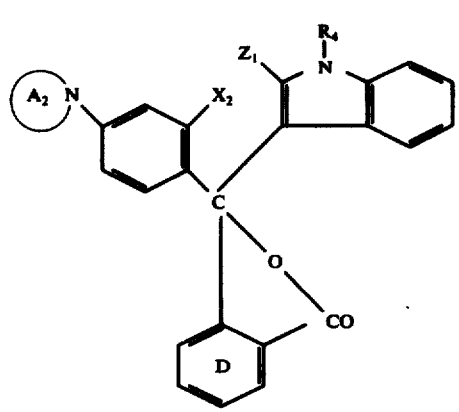

wherein

D, $X_2$ and $Z_1$ have the meanings given above, $R_4$ represents hydrogen, alkyl with 1 to 8 carbon atoms, acetyl or benzyl, and the nitrogen ring $A_2$ represents pyrrolidino, piperidino, morpholino or a N-alkyl-piperazino group having 1 to 4 carbon atoms in the alkyl part.

Among these compounds of formula (5) the compounds of the fomrula (6)

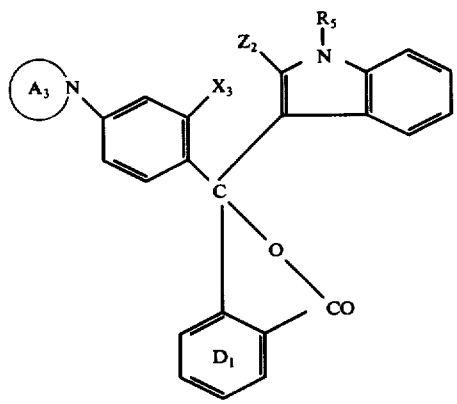

are more preferred, wherein $X_3$ represents methyl, methoxy, ethoxy or acetyloxy, $Z_2$ represents methyl or phenyl, $R_5$ represents hydrogen, alkyl with 1 to 8 carbon atoms or benzyl, the nitrogen ring $A_3$ represents pyrrolidino or piperidino and the benzene ring $D_1$ is unsubstituted or substituted by nitro or 1 to 4 chlorine or bromine atoms.

Within the above formulae (5) and (6) the benzene rings D and $D_1$, respectively, are preferably unsubstituted or contains advantageously four chlorine atoms or a nitro group. In case of a nitro substitution the phthalide compounds of formulae (5) and (6) are preferably mixtures of two isomers wherein the nitro groups of the phthalic anhydride residue are either in 4- and 7-positions or in the 5- and 6-positions.

The new lactone compounds of the formulae (1) to (6) are accessible by known methods. A process of manufacturing the lactone compounds of formula (1) comprises reactings in any order desired one mole of an anhydride compound of the formula (7)

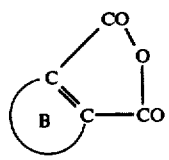

with one mole of a heterocyclic compound of the formula

Y—H (8)

, and one mole of a compound of the formula (9)

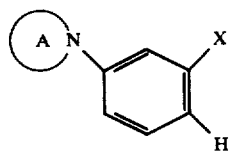

wherein A, B, X and Y have the meanings and X may also be hydroxy, and alkylating or acylating the reaction product when X is hydroxy.

Advantageously, the lactone compounds according to the invention are manufactured by reacting a compound of the formula (10)

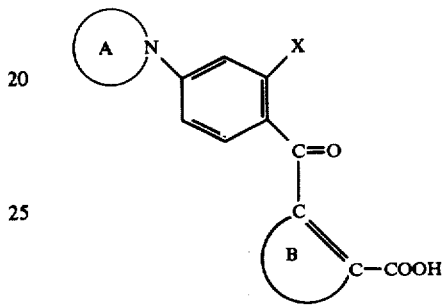

with a heterocyclic compound of the formula Y—H (8) wherein A, B, X and Y have the given meanings, and X may also be hydroxy, and alkylating or acylating the reaction product when X is hydroxy.

This reaction is desirably carried out by allowing the reactants to react together in the presence of an acidic dehydrating agent. Examples of suitable condensing agents are acetic anhydride, sulphuric acid and zinc chloride or phosphorus oxychloride. Alternatively, the lactone compounds according to the invention may be obtained by reacting a compound of the formula (11)

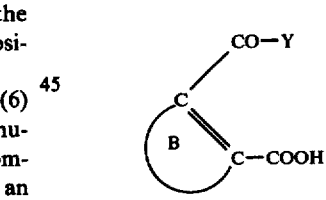

with a compound of the formula (9) and alkylating or acylating the reaction product when X is hydroxy.

The alkylation and acylation of the reaction products, wherein X is hydroxy are generally carried out by known methods e.g. in the presence of an acid binding agent such as an alkali metal carbonate, or a tertiary nitrogen base such as pyridine, and optionally in the presence of inert organic solvents such as acetone, isopropyl alcohol, chlorobenzene or nitrobenzene. Desirably, the alkylating and acylating agents contain at most 12 carbon atoms. Acylating agents which can be used here are e.g. reactive functional derivatives of aliphatic carboxylic acids, particularly fatty acid halides and anhydrides, such as acetyl bromide, acetyl chloride or acetic anhydride, or or aromatic carboxylic acids such as benzoic acid halides. Alkylating agents may be alkyl halides such as methyl or ethyl iodide or chloride, or dialkyl sulphates, such as dimethyl or diethyl sulphate.

The starting compounds of the formulae (10) and (11) are new or they are for example described in the British patent application No. 49331/73 corresponding to the Belgian Pat. No. 820305. Generally they are prepared by reacting an anhydride compound of the formula (7) with a compound of the formula (9) and with a heterocyclic compound of the formula (8), respectively, desirably in an organic solvent, optionally in the presence of a Lewis acid. Suitable organic solvents are for example benzene, toluene, xylene or chlorbenzene.

Among the Lewis acids aluminium chloride is preferred. The reaction is preferably carried out at temperatures at or below the boiling point of the solvents used. The compounds of formula (10), wherein X is alkoxy or acyloxy, are preferably obtained by alkylating or acylating, according to conventional methods as described above the intermediate products prepared by reacting an anhydride compound of the formula (7) with a compound of formula (9) wherein X is hydroxy. The acylating and alkylating agents may be the same, as described above for the manufacture of the final products of formula (1) and the subordinate formulae.

The compounds of formula (9) may be produced by condensing the heterocyclic base

in which the ring A has the meaning described above, with resorcinol or a monoalkyl or monoacyl ether derivative thereof or a metaalkylphenol at temperatures between 50° and 250° C and optionally under pressure. This reaction may or may not be assisted by the use of a condensing agent, examples of which are zinc chloride aluminium chloride or sulphanilic acid. Alternatively, the compounds of formula (9) may be prepared from the reaction of meta alkyl-, hydroxy-, alkoxy- or acyloxy-aniline with a $\alpha,\omega$-dihalogenoalkane in which the halogen is, for example, bromine or chlorine but more usually bromine.

The new lactones according to the invention are particularly useful as so-called colour formers. The term "colour former" is used to describe a compound which is normally colourless or very faintly coloured but which produces a strong colour when it is brought into contact with a co-reactive substrate which is an electron acceptor. Typical co-reactants are, for example, attapulgus clay, silton clay, silica, bentonite, halloysite, aluminium oxide, aluminium phosphate, kaolin or any acidic clay, or an acid reacting polymeric material such as a phenolic polymer, an alkylphenolacetylene resin, a maleic acid-rosin resin or a partially or wholly hydrolysed polymer of maleic anhydride with styrene, ethylene, vinyl methyl ether or carboxy polymethylenes.

The preferred co-reactants are attapulgus clay, silton clay, silica or a phenol-formaldehyde resin. These electron acceptors, preferably, are coated on the front side of the receiving sheet.

With the new colour formers according to the invention a large variety of green-blue, blue or violet-blue colours may be produced.

The present colour formers show an improved light-fastness, both on clay and phenolic substrates. With the present new lactones a further range of colour formers is provided with solubilities such as to allow greater flexibility in choice of solvents used for encapsulations and other modes of application.

Pressure-sensitive recording material may be of several kinds well known in the art and for example may consist of sheets of paper coated with microcapsules containing a solution of the colour formers. When these capsules are ruptured by pressure from writing, printing, or typing, the colour former is brought into contact with an acidic substance which is coated on the same or on an adjacent sheet thus producing an image which is a fine copy of the original.

The above example is only one of a variety of modes of application, the microcapsules may instead be contained in the base web or indeed as an alternative to encapsulation the solution of colour former may be protected from premature reaction by any other means such as entrapment in a foam-like layer or as an emulsion in a hardened film.

As already mentioned, these colour formers above all are suitable for the use in so-called pressure-sensitive copying or recording material. Such a material e.g. includes at least one pair of sheets, which comprises at least a colour former of formula (1) or of the surbordinate formulae dissolved in an organic solvent, preferably contained in pressure rupturable microcapsules and an electron accepting substance. The colour former, upon coming into contact with the electron accepting substance produces a coloured mark at the points where the pressure is applied.

These colour formers which are comprised in the pressure-sensitive copying material are prevented from becoming active by being separated from the electron accepting substance. This can be done by incorporating these colour formers into a foam-, sponge- or honeycomb-like structure. Preferably however the colour formers are microencapsulated.

When the capsules are ruptured by pressure from e.g. a pencil, and the colour former solution is thus transferred onto an adjacent sheet coated with a substrate capable of acting as an electron acceptor, a coloured image is produced. This colour results from the dyestuff thus produced, which absorbs in the visible region of the electromagnetic spectrum.

The general art of making microcapsules of some character has long been known. Well known methods e.g. are disclosed in U.S. Pat. Nos. 2,183,053, 2,797,201, 2,800,457, 2,800,458, 2,964,331, 3,016,308, 3,171,878, 3,265,630, 3,405,071, 3,418,250, 3,418,656, 3,424,827 and 3,427,250. Further methods are disclosed in British patent specifications Nos. 989,264 and above all 1,156,725, 1,301,052 and 1,355,124. Any of these and other methods are suitable for encapsulating the colour formers used according to the invention.

Preferably the colour formers are encapsulated dissolved in organic solvents. Suitable solvents are preferably non-volatile e.g. polyhalogenated diphenyl such as trichlorodiphenyl and its mixture with liquid paraffin, tricresyl phosphate, di-n-butyl phthalate, dioctyl phthalate, trichlorobenzene, nitrobenzene, trichloroethyl-phosphate, benzine, hydrocarbon oils, such as paraffin, alkylated derivatives or naphthalene or diphenyl, terphenyls, partially hydrogenated terphenyls, chlorinated or hydrogenated condensed aromatic hydrocarbons. The capsule walls can be obtained by coacervation forces evenly around the droplets of the colour former solution, wherein the encapsulating material may consist of gelatine, as e.g. described in U.S. Pat. No. 2,800,457.

Alternatively, the capsules preferably may be made of aminoplast or modified aminoplasts by polycondensation as described in British patent specification Nos. 989,264 or 1,156,725.

A preferred arrangement is wherein the encapsulated colour formed is coated on the back side of a transfer sheet and the electron accepting substance is coated on the front side of a receiving sheet.

In another preferred material the new lactones are co-encapsulated with one or more other known colour formers such as crystal violet lactone, 3,3-bis (1'-n-octyl-2'-methylindol-3'-yl)-phthalide or benzoyl leuco methylene blue.

The microcapsules containing the colour formers of formula (1) or of the subordinate formulae are used for making pressure-sensitive copying material of the various types known in the art. The various systems mainly are distinguished by the arrangement of the capsules, the colour reactants and the support material.

The microcapsules may be in a undercoating of the upper sheet and the colour reactants, that is the electron acceptor and coupler, may be in the overcoating of the lower sheets. However, the components may also be used in the paper pulp.

Another arrangement we have in the self-contained papers. There the microcapsules containing the colour former and the colour reactants are in or on the same sheet as one or more individual coatings or in the paper pulp.

Such pressure-sensitive copying materials are described e.g. in U.S. Pat. Nos. 3,516,846, 2,730,457, 2,932,582, 3,427,180, 3,418,250 and 3,418,656. Further systems are disclosed in British patent specifications Nos. 1,042,596, 1,042,597, 1,042,598, 1,042,599, 1,053,935 and 1,517,650. Microcapsules containing the colour formers of formula (1) are suitable for any of these and other systems.

The capsules are preferably fixed to the carrier by means of a suitable adhesive. Since paper is the preferred carrier material, these adhesives are predominantly paper coating agents, such as e.g. gum arabic, polyvinyl alcohol, hydroxymethylcellulose, casein, methylcellulose or dextrin.

In the present application, the definition "paper" not only includes normal papers from cellulose fibres, but also papers in which the cellulose fibres are replaced (partially or completely) by synthetic fibres of polymers.

The new lactone compounds may also be used as colour formers in thermoreactive recording material comprising at least a support, a colour former, an electron accepting substance and optionally a binder. Thermoreactive recording systems comprise heat-sensitive recording and copying materials and papers. These systems are used e.g. for the recording of information, for example, in electronic computers, in teleprinters or telewriters, in measuring instruments. The mark-forming also can be made manually with a heated pen. A further means for inducing heat-initiated marks are laser beams. The thermoreactive recording material may be arranged in such a manner that the colour former is dissoved or dispersed in a layer of the binder, and in a second layer the developer and the electron-accepting substance are dissolved or dispersed in the binder. Another possibility consists in dispersing both the colour former and the developer in one layer. By means of heat the binder is softened at specific areas imagewise and at these points where heat is applied, the colour former comes into contact with the electron-accepting substance and a colour is instantaneously formed.

The developers are the same electron-accepting substances as are used in pressure sensitive papers. Advantageously, the developer is solid at room temperature and melts or softens above 50° C. Examples of such products are the already mentioned clays, phenolic resins, phenolic compounds such as 4-tert.-butylphenol, 4-phenylphenol, 4-hydroxydiphenyloxide, α-naphthol, 4-hydroxybenzoic acid methyl ester, β-naphthol, 4-hydroxyacetophenone, 2,2'dihydroxydiphenyl, 4,4'-isopropyliden-diphenol, 4,4'-isopropyliden-bis-(2-methylphenol), 4,4'-bis-(hydroxyphenyl) valeric acid, hydroquinone, pyrogallol, phloroglucinol, p-, m-, o-hydroxybenzoic acid, gallic acid, 1-hydroxy-2-naphthoic acid, boric acid, and the aliphatic dicarboxylic acid e.g. tartaric acid, oxalic acid, maleic acid, citroaconic acid or succinic acid.

Preferably fusible, film-forming binders are used. These binders are generally water-soluble, whereas the lactones and the developer are water-insoluble. The binder should be able to disperse and fix the colour former and the developer at room temperature. After applying heat, the binder softens or melts, which enables the colour former to come into contact with the developer and to form a dyestuff.

Water-soluble or at least water-swellable binders are e.g. hydrophilic polymers such as polyviniyl alcohol, polyacrylic acid, hydroxyethylcellulose, methylcellulose, carboxymethylcellulose, polyacrylamide, polyvinylpyrrolidone gelatine or starch.

In so far as the colour former and the developer are coated in two separate layers, binders which are water insoluble may be used, i.e. binders soluble in non-polar or only weakly polar solvents, e.g. natural rubber, synthetic rubber, chlorinated rubber, alkyd resins, polystyrene, styrene-butadienecopolymers, polymethylmethacrylates, ethylcellulose, nitrocellulose or polyvinylcarbazole. The preferred arrangement, however, is colour former and developer in a water-soluble binder in one layer.

The coatings of the thermoreactive material may contain further additives. To improve the degree of whiteness, to ease the printing of the papers and to prevent the sticking of the heated pen, these materials may contain e.g. talc, $TiO_2$, ZnO or $CaCO_3$. In order to produce the dyestuff only within a limited temperature range there may be added substances such as urea, thiourea, acetanilide, phthalic acid anhydride or other corresponding meltable products which induce the simultaneous melting of colour former and developer.

Typical thermoreactive recording materials wherein the present colour formers may be used e.g. are described in German Patent Application No. 2,228,581, French Pat. No. 1,524,826, Swiss Pat. No. 407,185, German Patent Application 2,110,854, Swiss Pat. Nos. 164,976, 444,196 and 444,197.

The following non-limitative examples illustrate the present invention. Percentages are expressed by weight, unless otherwise stated.

EXAMPLE 1

3-(2'-Ethoxy-4'-N-pyrrolidinylphenyl)-3-(1'''-ethyl-2''-methylindol-3''-yl)-4,5,6,7-tetrachlorophthalide A mixture of 2,87 g N-(3'-ethoxyphenyl)pyrrolidine, 6,67 g 3-(2'-carboxy-3',4',5',6'-tetrachlorobenzoyl)-1-ethyl-2-methylindole and 7,7 g acetic anhydride is stirred for 4 hours at 125° C. After the addition of 1,1 ml water and 5 ml acetone at 80° C the mixture is cooled to 20° C to pecipitate a solid. The solid is filtered off, washed with methanol and dried. A colourless lactone is obtained in a yield which is 60% of the theory. M.p. 181° C from ethyl methyl ketone. A solution of this lactone in 95% acetic acid shows λmax at 595 nm. A solution of the lactone in toluene gives a deep blue colouration when it is contacted with attapulgus clay, silton clay or a phenolic resin.

EXAMPLE 2

3-(2'-Ethoxy-4'-N-pyrrolidinylphenyl)-3-(1''-n-propyl-2''-methylindol-3''-yl) phthalide A mixture of 0,865 g 1-n-propyl-2-methylindole, 1,695 g 2-(2'-ethoxy-4'-N-pyrrolidinylbenzoyl) benzoic acid and 5 ml acetic anhydride is stirred at 70° C for 1 hour, and 10 ml methanol is added. After cooling to 20° C the lactone which precipitates is filtered off, washed with methanol and dried to yield 2,18 g (88% of the theory) of white crystals. M.p. 218°–219,5° C from acetone-water.

A solution of the lactone in 95% acetic acid shows λmax at 579 nm. A solution of the lactone in toluene gives a deep violet-blue colouration when it is contacted with attapulgus clay or silton clay and deep blue on a phenolic resin.

of the examples 16 to 23 and 26 to 27 in Table II are isomeric mixtures having the nitro groups either in positions 4 and 7 or 5 and 6 of the phthalic anhydride residue. In the antepenultimate column of each table the observed λmax in 95% acetic acid are quoted. When brought into contact with silton clay or a phenolic resin the colour formers of formulae (12) and (13) develop the colours indicated in the last two columns of the tables.

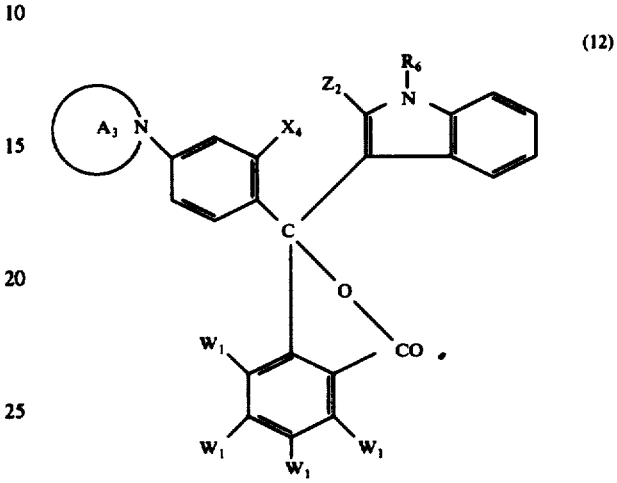

(12)

Table I

| Ex No | $A_3$ | $X_4$ | $Z_2$ | $R_6$ | $W_1$ | m.p. °C | λmax in 95% acetic acid | colour development by Silton clay | Phenolic resin |
|---|---|---|---|---|---|---|---|---|---|
| 4 | N-pyrrolidinyl | —OC$_2$H$_5$ | CH$_3$ | —C$_2$H$_5$ | H | 217–218 | 578 nm | violet-blue | blue |
| 5 | " | " | CH$_3$ | n-C$_4$H$_9$ | H | 186–187 | 579 | " | " |
| 6 | " | " | CH$_3$ | n-C$_6$H$_{13}$ | H | 114–115 | 580 | " | " |
| 7 | " | " | CH$_3$ | n-C$_8$H$_{17}$ | H | 141–142 | 580 | " | " |
| 8 | " | —OCOCH$_3$ | CH$_3$ | —C$_2$H$_5$ | H | 206–207 | 599 | blue | turquoise blue |
| 9 | " | —CH$_3$ | CH$_3$ | —C$_2$H$_5$ | Cl | 124–127 | 625 | " | " |
| 10 | N-piperidino | —OCH$_3$ | CH$_3$ | —C$_2$H$_5$ | Cl | 118–124 | 601 | " | blue |
| 11 | N-pyrrolidinyl | —OCOCH$_3$ | CH$_3$ | —C$_2$H$_5$ | Cl | 234–235 | 625 | " | turquoise blue |
| 12 | " | " | CH$_3$ | —C$_2$H$_5$ | Br | >260 d | 624 | " | green |
| 13 | " | —OC$_2$H$_5$ | CH$_3$ | —COCH$_3$ | H | 233–235 | 570 | violet-blue | violet-blue |
| 14 | " | " | —⟨phenyl⟩ | n-C$_7$H$_{15}$ | H | 93–95 | 585 | blue | blue |
| 15 | " | " | CH$_3$ | —CH$_2$—⟨phenyl⟩ | H | 212–214 | 575 | violet-blue | " |

EXAMPLE 3

3-(2'-Acetoxy-4'-N-pyrrolidinylphenyl)-3-(1''-n-hexyl-2''-methylindol-3''-yl phthalide A mixture of 1,075 g 1-n-hexyl-2-methylindole, 1,555 g 2-(2'-hydroxy-4'-N-pyrrolidinylbenzoyl) benzoic acid and 4 ml acetic anhydride is stirred at 70° C for 2 hours and 15 ml methanol is added. After cooling to 20° C the product obtained is filtered off, washed with methanol and dried to yield 2,3g (84% of the theory) of the lactone as a white solid. M.p. 124°–125° C from methanol. A solution of the lactone in 95% acetic acid shows λmax at 600 nm. A solution of the lactone in toluene gives a blue colouration when it is contacted with attapulgus or silton clay and a turquoise-blue on a phenolic resin.

According to substantially the same procedures as described in any one of the Examples 1 to 3, the following compounds of the formulae (12) and (13) given in the Tables I and II below are obtained. The compounds

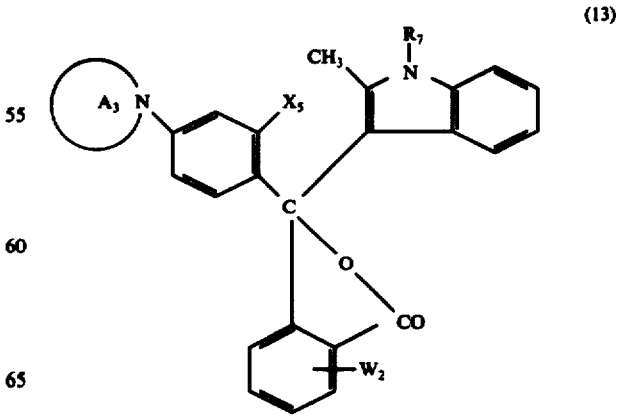

(13)

Table II

| Ex No | $A_3$ | $X_5$ | $R_7$ | $W_2$ | m.p. °C | λmax in 95% acetic acid | colour development by Silton clay | colour development by Phenolic resin |
|---|---|---|---|---|---|---|---|---|
| 16 | N-pyrrolidinyl | —OCOCH$_3$ | n-C$_3$H$_7$ | 4-and 7-nitro | 236d. | 614 | blue | turquoise-blue |
| 17 | " | —OCOCH$_3$ | —C$_2$H$_5$ | 5-and 6-nitro | 152–156 | 618 | blue | green |
| 18 | " | —CH$_3$ | —C$_2$H$_5$ | 4-and 7-nitro | 251d. | 613 | blue | blue |
| 19 | " | —CH$_3$ | —C$_2$H$_5$ | 5-and 6-nitro | 249–250 | 620 | turquoise blue | turquoise-blue |
| 20 | N-piperidino | —OCH$_3$ | —C$_2$H$_5$ | 4-and 7-nitro | 121–124 | 590 | blue | blue |
| 21 | " | —OCH$_3$ | —C$_2$H$_5$ | 5-and 6-nitro | 141–144 | 590 | blue | blue |
| 22 | " | CH$_3$ | n-C$_3$H$_7$ | 4-and 7-nitro | 164–167 | 616 | blue | blue |
| 23 | " | —CH$_3$ | n-C$_6$H$_{13}$ | 5-and 6-nitro | 108–112 | 619 | turquoise blue | green |
| 24 | N-pyrrolidinyl | —OCH$_3$ | n-C$_3$H$_7$ | 4-nitro | 128–130 | 586 | blue | blue |
| 25 | " | " | " | 7-nitro | 191-194 | 588 | blue | blue |
| 26 | " | " | n-C$_4$H$_9$ | 5-and 6-nitro | 128–135 | 591 | blue | blue |
| 27 | " | " | n-C$_6$H$_{13}$ | 5-and 6-nitro | 119–126 | 592 | blue | blue |

EXAMPLE 28

A mixture of 0,407 g 1-ethyl-2-methylindole, 0,78 g 2-(2'-hydroxy-4'-N-pyrrolidinylbenzoyl) picolinic acid and 4 ml acetic anhydride is stirred at 70° C for 2 hours and 15 ml methanol is added. After cooling to 20° C the product obtained is filtered off, washed with methanol and dried to yield 0,56 g of the lactone of the formula

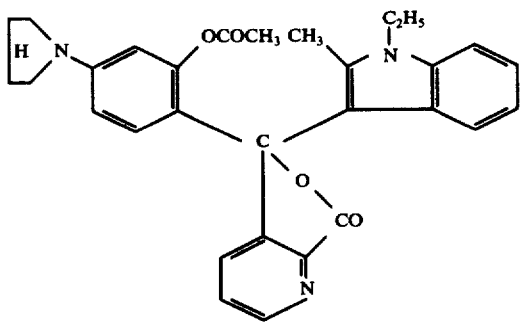

(14)

as a white solid M.p. 159°-162° C. A solution of the lactone in 95% acetic acid shows λ max at 612 nm. A solution of the lactone in toluene gives a blue colouration when it is contacted with attapulgus or silton clay and a turquoise-blue on a phenolic resin.

EXAMPLE 29

A mixture of 1,59 g 1-ethyl-2-methylindole, 3,89 g 2-(2'-ethoxy-4'N-pyrrolidinylbenzoyl) naphthoic acid and 5 ml acetic anhydride is stirred at 70° C for 1 hour, and 10 ml methanol is added. After cooling to 20° C the lactone which precipitates is filtered off, washed with methanol and dried to yield 4,72 g of a compound of the formula (15)

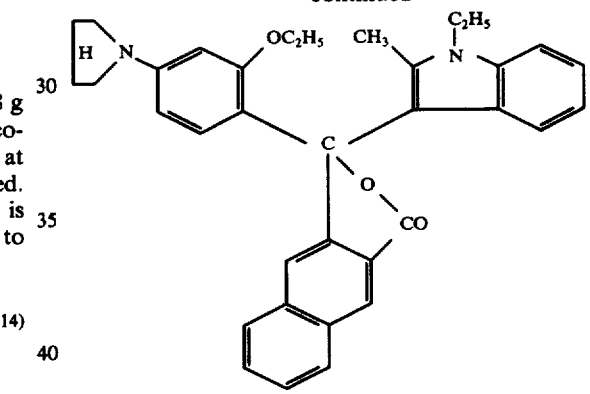

having a melting point at 200°-221° C. A solution of the lactone in 95% acetic acid shows λ max at 578 and 415 nm. A solution of the lactone in toluene gives a deep violet-blue colouration when it is contacted with attapuglus clay or silton clay and deep blue on a phenolic resin.

EXAMPLE 30

3-(2'-Acetoxy-4'-N-pyrrolidinylphenyl)-3(1"-ethyl-2"-methyl-indol-3"-ylnapththalide A mixture of 0,795 g 1-ethyl -2-methylindole, 1,805 g 2-(2'-hydroxy-4'-N-pyrrolidinylbenzoyl) naphthoic acid and 4 ml acetic anhydride is stirred at 70° C for 2 hours and 15 ml methanol is added. After cooling to 20° C the product obtained is filtered off, washed with methanol and dried to yield 1,85 g (68% of the theory) of the lactone as a white solid. M.p. 243°C from methanol. A solution of the lactone in 95% acetic acid shows λ max at 597 and 434 nm. A solution of the lactone in toluene gives a blue colouration when it is contacted with attapulgus or silton clay and a green on a phenolic resin.

APPLICATION EXAMPLES

EXAMPLE 31

Preparation of pressure-sensitive copying paper

A solution of 3 g of 3-(2'-ethoxy-4'-N-pyrrolidinyl-phenyl)-3-(1''-n-propyl-2''-methylindol-3''-yl)phthalide according to Example 2 in 97 g of hydrogenated terphenyl is emulsified in a solution of 12 g of pigskin gelatine in 88 g of water at 50° C, then a solution of 12 g gum arabic in 88 g of water at 50° C is added. The emulsion is diluted by adding 200 ml of water at 50° C and coacervation is brought about by pouring into 600 g of ice-water and stirring for 3 hours. The resulting suspension is coated on paper and dried. When this paper is placed with its coated side adjacent to a sheet of paper coated either with attapulgus clay, silton clay, silica, or phenolic resin and writing or typing is made upon the top sheet, a strong blue copy is made upon the co-reactive sheet. Similar effects can be obtained by using any other colour former as listed in the Examples 1 and 3 to 30.

EXAMPLE 32

Preparation of pressure-sensitive copying paper

A solution of 1,8 g of 3-(2'-acetoxy-4'-N-pyrrolidinyl-phenyl)-3(1''-n-hexyl-2'-methylindol-3''-yl)-phthalide according to Example 3 and 1,5 g benzoyl leuco methylene blue in 97 g of hydrogenated terphenyl is emulsified in a solution of 12 g of pigskin gelatine in 88 g of water at 50° C then a solution of 12 g gum arabic in 88 g of water at 50° C is added. The emulsion is diluted by adding 200 ml of water at 50° C and coacervation is brought about by pouring into 600 g of ice-water and stirring for 3 hours. The resulting suspension is coated on paper and dried. When this paper is placed with its coated side adjacent to a sheet of paper coated either with attapulgus clay, silton clay, or silica, and writing or typing is made upon the top sheet, a strong blue copy is made upon the co-reactive sheet. Similar effects can be obtained by using any other colour former listed in the Examples 1, 2 and 4 to 30.

EXAMPLE 33

Preparation of thermoreactive paper 6 g of an aqueous dispersion containing 1,57% of a colour former according to Example 2 and 6,7% of polyvinyl alcohol are mixed with 134 g of an aqueous dispersion containing 14% 4,4'-isopropylidene-diphenol and 6% polyvinyl alcohol, and is coated on paper and dried. When contacted with a heated stylus a strong blue mark is obtained which has an excellent fastness to light.

Similar effects can be obtained by using any other colour former listed in the Examples 1 and 3 to 30.

We claim:
1. A lactone compound of the formula

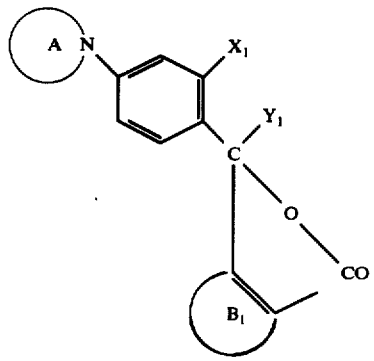

wherein
X$_1$ is alkyl of 1 to 4 carbon atoms, alkoxy of 1 to 8 carbon atoms, or acyloxy of 2 to 8 carbon atoms selected from the group consisting of akyl carboxylic acid acyloxy and benzoyloxy;
Y$_1$ represents

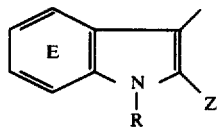

wheren
R is hydrogen, alkyl of 1 to 12 carbon atoms, alkenyl of up to 12 carbon atoms, alkanoyl of 2 to 4 carbon atoms, phenyl, benzyl or phenyl or benzyl which are substituted by halo, nitro, methyl or methoxy;
Z is hydrogen, alkyl of 1 to 12 carbon atoms or phenyl;
and the benzene ring E is unsubstituted or substituted by alkyl of 1 to 4 carbon atoms, alkoxy of 1 to 4 carbon atoms, halo or nitro;
the ring B, represents naphthalene, benzene or benzene substituted by chloro, bromo or nitro; and
the ring A represents pyrrolidinyl, piperidino, pipecolino, perhydroazepinyl, hexamethyleneiminyl, heptamethylene-iminyl, octamethyleneiminyl, 1,2,3,4-tetrahydroquinolinyl indolinyl, phthalimidinyl, hexahydrocarbozolyl.

2. A compound according to claim 1, wherein the ring A represents piperidino or pyrrolidinyl.

3. A compound according to claim 2 of the formula

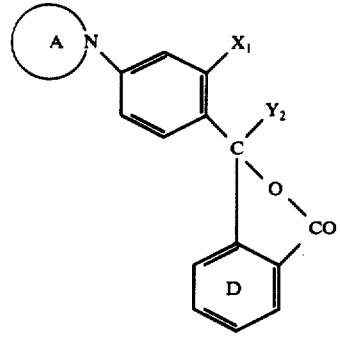

wherein Y$_2$ is

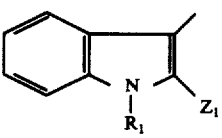

where
R$_1$ is hydrogen, alkyl of 1 to 12 carbon atoms, alkanoyl of 2 of 4 carbon atoms or benzyl;
Z$_1$ represents hydrogen, alkyl of 1 to 4 carbon atoms or phenyl; and
the benzene ring D is unsubstituted or substituted by nitro or 1 to 4 halo.

4. A lactone compound to claim 3, of the formula

-continued

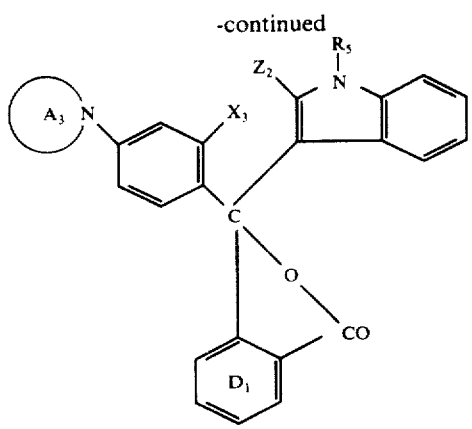

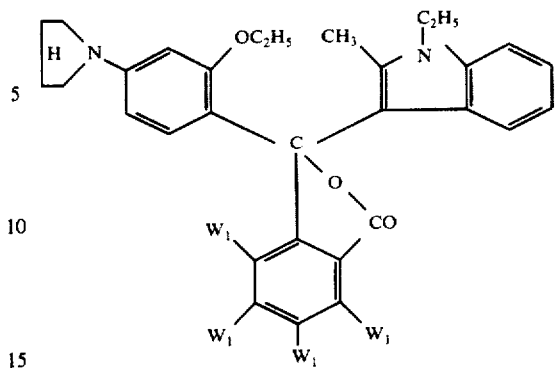

wherein
X₃ represents methyl, methoxy, ethoxy or acetyloxy,
Z₂ represents methyl or phenyl,
R₅ represents hydrogen, alkyl with 1 to 8 carbon atoms or benzyl,
the nitrogen ring A₃ represents pyrrolidino or piperidino and the benzene ring D₁ is unsubstituted or substituted by nitro or 1 to 4 chlorine or bromine atoms.

5. A lactone compound according to claim 4, wherein the benzene ring D₁ is unsubstituted or contains four chlorine atoms or a nitro group.

6. A lactone compound according to claim 4, which is a mixture of two isomers wherein the phthalic anhydride residue is of the formula

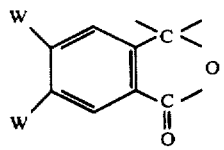

wherein one W is nitro and the other W is hydrogen.

7. A lactone compound according to claim 4, which is a mixture of two isomers wherein the phthalic anhydride residue is of the formula

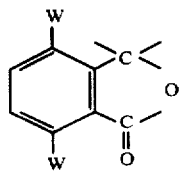

wherein one W is nitro and the other W is hydrogen.

8. A lactone compound according to claim 4, of the formula wherein $W_1$ is hydrogen or chlorine.

9. A lactone compound according to claim 8, wherein W1 is hydrogen.

10. A lactone compound according to claim 4, of the formula

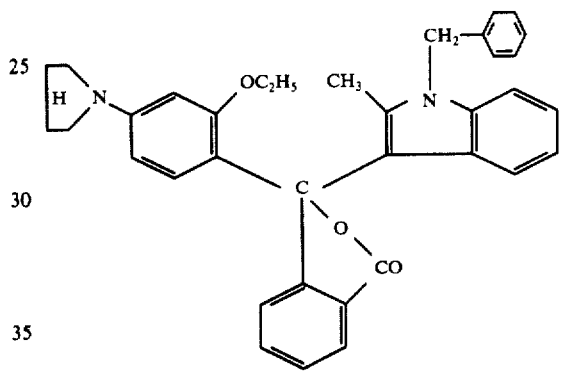

11. A lactone compound according to claim 4, of the formula

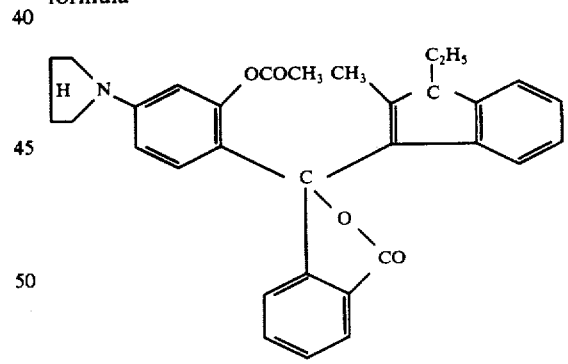

* * * * *